US010695379B2

(12) United States Patent
Greenwood et al.

(10) Patent No.: US 10,695,379 B2
(45) Date of Patent: Jun. 30, 2020

(54) CELL POPULATION SEEDING IN DERMAL MATRICES FOR ENDOCRINE DISORDER MANAGEMENT

(71) Applicant: BETA CELL TECHNOLOGIES PTY LTD, Parkside, South Australia (AU)

(72) Inventors: John Greenwood, Parkside (AU); Patrick Toby Hewlett Coates, Parkside (AU)

(73) Assignee: BETA CELL TECHNOLOGIES, PTY LTD, South Australia (AU)

( * ) Notice: Subject to any disclaimer, the term of this patent is extended or adjusted under 35 U.S.C. 154(b) by 41 days.

(21) Appl. No.: 15/763,931

(22) PCT Filed: Oct. 19, 2017

(86) PCT No.: PCT/AU2017/051134
§ 371 (c)(1),
(2) Date: Mar. 28, 2018

(87) PCT Pub. No.: WO2018/071975
PCT Pub. Date: Apr. 26, 2018

(65) Prior Publication Data
US 2019/0054124 A1 Feb. 21, 2019

(30) Foreign Application Priority Data

Oct. 19, 2016 (AU) ................................ 2016904244

(51) Int. Cl.
| *A61K 35/39* | (2015.01) |
| *A61L 27/56* | (2006.01) |
| *A61K 38/28* | (2006.01) |
| *A61L 27/38* | (2006.01) |
| *A61P 3/10* | (2006.01) |
| *A61L 27/18* | (2006.01) |
| *A61L 27/54* | (2006.01) |
| *A61L 27/58* | (2006.01) |
| *A61K 9/70* | (2006.01) |
| *A61K 9/00* | (2006.01) |
| *A61K 45/06* | (2006.01) |
| *A61L 26/00* | (2006.01) |

(52) U.S. Cl.
CPC ............ *A61K 35/39* (2013.01); *A61K 9/0019* (2013.01); *A61K 9/70* (2013.01); *A61K 38/28* (2013.01); *A61K 45/06* (2013.01); *A61L 26/0019* (2013.01); *A61L 27/18* (2013.01); *A61L 27/3804* (2013.01); *A61L 27/3834* (2013.01); *A61L 27/54* (2013.01); *A61L 27/56* (2013.01); *A61L 27/58* (2013.01); *A61P 3/10* (2018.01); *A61L 2300/414* (2013.01); *A61L 2300/426* (2013.01); *A61L 2300/43* (2013.01); *A61L 2300/64* (2013.01); *A61L 2400/06* (2013.01)

(58) Field of Classification Search
CPC combination set(s) only.
See application file for complete search history.

(56) References Cited

U.S. PATENT DOCUMENTS

2006/0153894 A1    7/2006   Ghabrial et al.

FOREIGN PATENT DOCUMENTS

| EP | 1466633 A1 | 10/2004 | |
| WO | 2005005609 A2 | 1/2005 | |
| WO | WO-2006066882 A2 * | 6/2006 | ........... A61L 31/048 |
| WO | 2009131752 A2 | 10/2009 | |
| WO | WO-2001025977 A2 * | 3/2011 | ............. A61L 27/16 |
| WO | 2001130322 A1 | 10/2011 | |
| WO | 2012130567 A1 | 10/2012 | |

OTHER PUBLICATIONS

Swinnen et al. Insulin Therapy for Type 2 Diabetes. Diabetes Care, vol. 32, Supplement 2, Nov. 2009. p. S253-S259 (Year: 2009).*
Wherrett et al. Prevention of type 1 diabetes. Endocrinol Metab Clin North Am. Dec. 2009 ; 38(4): 777-790 (Year: 2009).*
American Diabetes Association. Prevention of Type 1 Diabetes Mellitus. Diabetes Care, vol. 26, Supplement 1 , Jan. 2003. p. S140 (Year: 2003).*
O'Cearbhaill et al. Emerging Medical Devices for Minimally Invasive Cell Therapy. Mayo Clin Proc. 2014;89(2):259-273 (Year: 2014).*
Ronald J. Pettis, Ph.D, et al.; Intradermal Microneedle Delivery of Insulin Lispro Achieves Faster Insulin Absorption and Insulin Action than Subcutaneous Injection; Diabetes Technology & Therapeutics; vol. 13, No. 4, 2011; 8 Pages.
Lutz Heinemann, PhD; Future Directions in Insulin Therapy and Treatment of Diabetes Mellitus: A Critical Comment; Clinical Cornerstone; Insulin Therapy in Type 2 Diabetes; vol. 8, No. 2; 66 Pages.
Steven Keith; DiabetesPro; Compartmental Modeling of Intradermal and Subcutaneous Insulin Delivery; 2010; Abstract No. 540-P; 2 Pages.
Fotino, N. et al.; "Re-engineering islet cell transplantation" Pharmacological Research, 2015, vol. 98, pp. 76-85; pp. 78-80.

* cited by examiner

*Primary Examiner* — Taeyoon Kim
(74) *Attorney, Agent, or Firm* — Renner Kenner Greive Bobak Taylor & Weber (57) ABSTRACT

A method of delivering a cell derived factors to a subject is described, which includes implanting a matrix material into an intracutaneous location in the subject that results in increased vascularisation and subsequently efficient delivery of the required cell derived factors to the subject. The implanted matrix material can be loaded in-situ or alternatively pre-loaded and inserted into the appropriate location depending on requirements.

31 Claims, 4 Drawing Sheets

CELL POPULATION SEEDING IN DERMAL MATRICES FOR ENDOCRINE DISORDER MANAGEMENT

FIELD

The present disclosure relates to methods and products for delivering a cell derived factor to a subject.

BACKGROUND

Cellular therapy has become recognised as a new treatment modality for some diseases, particularly for diseases which are caused by loss of or damage to cells producing factors necessary for control of physiological functions. Cellular therapy holds the promise of replacing lost or damaged cells with introduced cells to improve the impaired physiological functions. For example, transplantation of islets of Langerhans cells has the potential for restoring carbohydrate control in patients with diabetes.

Cellular therapy has a variety of limitations. For example, one limiting factor is the difficulty in transplanting cells and ensuring that the transplanted cells continue to function as they would in their natural state. In addition, the introduction of non-autologous (allogeneic or xenogeneic) cells will typically elicit an immune response, requiring immunosuppressant therapy as well.

For example, whilst the use of Clinical Islet Transplantation using hepatic portal vein introduction of islet cells can achieve insulin independence rates of ~80% at 1 year, the procedure still requires multiple islet infusions over time and immunosuppressive therapy. The direct exposure of the cells to the blood may also lead to an inflammatory reaction that can destroy a significant portion of the transplanted cells and the procedure carries a significant risk of portal vein thrombosis.

An alternative approach for cellular therapy has been to deliver cells using devices that attempt to provide a biologically suitable environment for the cells to reside. However, this type of approach typically results in a rapid loss of cell function. This type of approach also suffers from a variety of other deficiencies, such as one or more of an induction of an inflammatory response when the device is introduced into the host, an incompatibility of the device with the biological milieu, difficulties in imaging the device and/or the implantation environment, difficulties with loading the device with cells, the need to surgically load (and re-load) the cells, an inability to load an appropriate number of cells for a sustained therapeutic effect, and a difficulty in removing the device if/when it needs replacement.

Accordingly, there remains a need for improved methods of cellular therapy.

SUMMARY

Certain embodiments of the present disclosure provide a method of delivering a cell derived factor for therapy to a subject, the method comprising:
  implanting a matrix into a site in the subject to allow neovascularisation of the site with the implanted matrix; and
  introducing cells producing a cell derived factor into the site, thereby delivering the cell derived factor to the subject from the cells introduced into the site.

Certain embodiments of the present disclosure provide a method of preventing and/or treating diabetes, pre-diabetes or insulin resistance in a subject, the method comprising:
  implanting a matrix into a site in the subject to allow neovascularisation of the site with the implanted matrix; and
  introducing cells producing insulin into the site, thereby preventing and/or treating the subject by delivering the insulin produced from the cells to the subject in physiologically relevant doses.

Certain embodiments of the present disclosure provide a method of delivering a cell derived factor to a subject, the method comprising:
  implanting a biodegradable matrix into an intracutaneous and/or dermal site in the subject;
  allowing neovascularisation of the site with the implanted matrix to form a neovascularised site; and
  introducing cells producing a cell derived factor into tissue into the site, thereby delivering the cell derived factor to the subject produced from the cells introduced into the site.

Certain embodiments of the present disclosure provide a method of delivering a cell derived factor to a subject, the method comprising:
  creating an open intracutaneous and/or an open dermal site in the subject;
  implanting a biodegradable matrix into the open intracutaneous and/or open dermal site in the subject, wherein the matrix further comprises a non-biodegradable seal to close the site upon implantation of the matrix;
  allowing neovascularisation of the site with the implanted matrix to form a neovascularised site; and
  introducing cells producing a cell derived factor into tissue in the neovascularised site, thereby delivering the cell derived factor to the subject produced from the cells introduced into the site.

Certain embodiments of the present disclosure provide a method of preventing and/or treating diabetes, pre-diabetes or insulin resistance in a subject, the method comprising:
  implanting a biodegradable matrix into an intracutaneous and/or dermal site in the subject;
  allowing neovascularisation of the site with the implanted matrix to form a neovascularised site; and
  introducing cells producing insulin into tissue in the neovascularised site, thereby delivering the insulin to the subject produced from the cells introduced into the site.

Certain embodiments of the present disclosure provide a method of preventing and/or treating diabetes, pre-diabetes or insulin resistance in a subject, the method comprising:
  creating an open intracutaneous and/or an open dermal site in the subject;
  implanting a biodegradable matrix into the open intracutaneous and/or open dermal site in the subject, wherein the matrix further comprises a non-biodegradable seal to close the site upon implantation of the matrix;
  allowing neovascularisation of the site with the implanted matrix to form a neovascularised site; and
  introducing cells producing insulin into tissue in the neovascularised site, thereby delivering the insulin to the subject produced from the cells introduced into the site.

Certain embodiments of the present disclosure provide use of a biodegradable matrix for implantation into a subject for preventing and/or treating diabetes, pre-diabetes or insulin resistance in the subject.

Certain embodiments of the present disclosure provide a kit for delivering a cell derived factor to a subject, the kit comprising a biodegradable matrix that when implanted into a site in the subject allows neovascularisation of the site and optionally one or more reagents and/or devices for preparing and/or delivering cells that produce a cell derived factor to the site.

Certain embodiments of the present disclosure provide a non-human animal comprising exogenous cells introduced into a neovascularised site in the animal, the cells producing, or capable of producing, a cell derived factor, and wherein the neovascularised site is formed by implanting a biodegradable matrix into the site and allowing neovascularisation of the site with the implanted matrix.

The terms 'intracutaneous' and 'intradermal' as used herein refer to the region of the epidermal layer and/or dermal layer of the skin (within the skin), specifically excluding the subcutaneous layer.

The term "matrix" as used herein refers to a scaffold or frame that is used to provide support in the neovascularised site. The scaffold or frame is formed from a material or materials as described herein, but not necessarily limited to.

The term "neovascularised" or "neovascularisation" refers to the formation of new blood vessels, usually in the form of a micro-vascular network of blood vessels that are capable of allowing blood cells to travel within.

Other embodiments as described herein.

BRIEF DESCRIPTION OF THE FIGURES

Exemplary embodiments will be better understood and appreciated in conjunction with the following detailed description of example embodiments taken together with the accompanying figures. It is to be understood that the following description of the figures is for the purpose of describing example embodiments only and is not intended to be limiting with respect to this disclosure.

FIGS. 2 A, B and C show visualisation of human islets after 7 days of islet transplantation into pre-vascularised matrix material.

DETAILED DESCRIPTION

The present disclosure relates to methods and products for delivering cell derived factors to a subject.

Certain embodiments of the present disclosure are directed to methods and products. For example, some of the advantages of the embodiments disclosed herein include one or more of the following: the use of a non-hepatic route for implanting pancreatic beta cells or islets of Langerhans cells; use of a biodegradable and non-toxic matrix to implant cells; a method that forms a site in a subject suitable for introduction of cells; a method of implanting cells that allows ease of biopsy and/or monitoring; a method of implanting cells that provides improved access for in vive imaging of graft mass; a method of implanting cells that provides complete retrieval of implanted cells if necessary; a method of cell transplantation that can be performed under minimal sedation as an outpatient procedure; a method of implanting cells that may provide subsequent significant cost savings associated with treatment; a method of treatment of diabetes that may allow a reduction in the number of islet infusions required for insulin independence; a method of implanting cells that allows for local application of drugs; to provide one or more advantages; or to provide a commercial alternative. Other advantages of certain embodiments of the present disclosure are also disclosed herein.

The present disclosure is based upon the recognition that a matrix which supports vascularisation when implanted into a subject forms a vascularised, non-inflamed environment into which pancreatic beta cells or islets of Langerhans cells may be transplanted and thereby provide insulin to the subject. The ability to introduce cells producing a cell derived factor into a vascularised, non-inflamed environment provides a new methodology to deliver cell derived factors to a subject.

Certain embodiments of the present disclosure provide a method of delivering a cell derived factor to a subject.

Certain embodiments of the present disclosure provide a method of delivering a cell derived factor to a subject, the method comprising:

implanting a matrix into a site in the subject to allow neovascularisation of the site with the implanted matrix; and introducing cells producing a cell derived factor into the site;

thereby delivering the cell derived factor to the subject from the cells introduced into the site.

In certain embodiments, the cell derived factor comprises one or more of a peptide hormone, a hormone, a cytokine, a growth factor and a chemokine, and/or a precursor, an immature form, or a pre-processed form of any of the aforementioned. Other types of cell derived factors are contemplated.

In certain embodiments, the cell derived factor is an endocrine factor.

In certain embodiments, the cell derived factor is a naturally-produced factor. In certain embodiments, the cell derived factor is a recombinant factor.

In certain embodiments, the cell derived factor is a syngeneic factor. In certain embodiments, the cell derived factor is an allogeneic factor. In certain embodiments, the cell derived factor is a xenogeneic factor.

In certain embodiments, the factor comprises insulin.

The term "subject" as used herein refers to a human or animal subject.

In certain embodiments, the subject is a mammalian subject, a livestock animal (such as a horse, a cow, a sheep, a goat, a pig), a domestic animal (such as a dog or a cat) or other type of animal such as a primate, a rabbit, a rat, a mouse, a bird and a laboratory animal. Other types of animals are contemplated. Veterinary applications of the present disclosure are contemplated. Animal models are contemplated.

In certain embodiments, the subject is a human subject.

In certain embodiments, the subject is suffering from, or susceptible to, a disease, condition or state that would benefit from the delivery of cells to the subject.

For example, the method may be used in treatment regimes that are beneficial for diabetes, pre-diabetes or insulin resistance. In certain embodiments, the method may be used in a subject undergoing pancreatectomy.

In certain embodiments, the cells for introduction comprise syngeneic cells. In certain embodiments, the cells comprise allogeneic cells. In certain embodiments, the cells comprise xenogeneic cells. Methods for isolating syngeneic, allogeneic and xenogeneic cells are known in the art.

In certain embodiments, the cells comprise a cell that produces the cell derived factor, or a progenitor cell type that produces, or is capable of producing, the cell derived factor. For example, pluripotent stem cells or other progenitor cells may be produced which form beta cells, such as described in Rezania et al. (2014) *Nat Biotechnol.* 32(11):1121-33, Pagliuca et al. (2014) *Cell* 159(2):428-39, and Kroon et al. (2008) *Nat Biotechnol.* 26(4):443-52.

In certain embodiments, the cells comprise islets of Langerhans cells, pancreatic beta cells and/or a progenitor thereof. Other types of cells are contemplated.

In certain embodiments, the cells are isolated from the host into which they are to be introduced (syngeneic cells). In certain embodiments, the cells are isolated from an allogenic donor (allogeneic cells). In certain embodiments, the cells are isolated from a xenogenic donor (xenogeneic cells).

In certain embodiments, the cells comprise in vitro propagated cells.

In certain embodiments, the cells comprise natural cells. In certain embodiments, the cells comprise engineered cells. In certain embodiments, the cells comprise an exogenous nucleic acid. In certain embodiments, the cells comprise a recombinant nucleic acid. In certain embodiments, the cells comprise reduced expression of one or more antigens.

In certain embodiments, the site comprises one or more of an intradermal site, an intramuscular site, a site in the omentum, and a site in the mesentery of the gut and the abdominal wall. In certain embodiments, the site comprises one or more of an intradermal site, or an intramuscular site. Other types of sites for introduction of cells are contemplated.

The term "matrix" as used herein refers to a solid or a semi-solid substrate, carrier or scaffold, which may be biodegradable or permanent and which supports the formation of new blood vessels when implanted and/or is replaceable (partially or fully) by vascularised tissue when implanted In certain embodiments, the matrix comprises a synthetic matrix. In certain embodiments, the matrix comprises a natural matrix, or a matrix derived from a natural product. In certain embodiments, the matrix comprises a combination of synthetic and natural (biological) components.

In certain embodiments, the matrix is formed from one or more polymers.

Examples of matrices include a solid matrix, a semi-solid matrix, a gel matrix, a porous matrix, a fibrous matrix, a mat, a mesh, a sponge, or a foam. Other types of matrix are contemplated.

In certain embodiments, the matrix comprises a porous matrix.

In certain embodiments, the matrix comprises an average pore size of 100 µm or greater, 200 µm or greater, 300 µm or greater, 400 µm or greater, 500 µm or greater, 600 µm or greater, 700 µm or greater, 800 µm or greater, 900 µm or greater, or 1000 µm or greater.

Methods for determining pore size are known in the art. In certain embodiments, the pore size comprises the size of the largest cross sectional diameter of a pore.

In certain embodiments, the matrix is biodegradable. Biodegradable matrices are described, for example, in Calandrelli L et al. (2000) *Polymer* 41(22):8027-8033. In certain embodiments, the biodegradable matrix has a half life in vivo (for example as measured by the mass retained) of 10 to 120 days, 20 to 120 days, 30 to 120, 10 to 90 days, 20 to 90 days, 30 to 90 days, 10 to 30 days, 20 to 30 days or 10 to 20 days.

In certain embodiments, the matrix comprises a biodegradable polymer.

In certain embodiments, the matrix comprises a biodegradable polyurethane.

Polyurethane polymers, and methods for their production, are described for example, in international patent publications WO 2008/014561, WO 2009/043099, WO 2005/089778, WO/2004/009227 and WO/2005/085312, the contents of which are each hereby incorporated by reference in their entirety.

In certain embodiments, the introducing of the cells occurs after neovascularisation of the site. Methods for assessing vascularisation are known in the art.

In certain embodiments, the introducing of the cells occurs prior to vascularisation of the site. In certain embodiments, the introducing of the cells occurs during vascularisation of the site.

In certain embodiments, the site is partially or substantially vascularised at the time of introducing the cells. In certain embodiments, the site is partially vascularised at the time of introducing the cells. In certain embodiments, the site is substantially vascularised at the time of introducing the cells.

In certain embodiments, the matrix is partially or substantially replaced with tissue at the time of introduction of the cells.

In certain embodiments, the matrix is partially or substantially replaced with neovascularised tissue at the time of introduction of the cells.

In certain embodiments, the cells are introduced into the site 0 to 90 days after implantation of the matrix.

In certain embodiments, the cells are introduced into the site 0 to 90 days, 0 to 75 days, 0 to 60 days, 0 to 45 days, 0 to 30 days, 0 to 15 days, 15 to 90 days, 15 to 75 days, 15 to 60 days, 15 to 45 days, 15 to 30 days, 30 to 90 days, 30 to 75 days, 30 to 60 days, 30 to 45 days, 45 to 90 days, 45 to 70 days, 45 to 60 days, 60 to 90 days, 60 to 75 days or 75 to 90 days after implantation of the matrix. Other time periods are contemplated.

In certain embodiments, the cells are assessed for one or more of number, viability and sterility prior to implantation.

In certain embodiments, the matrix is implanted in the site for more than 30 days.

In certain embodiments, the matrix is partially or substantially innervated and vascularised, at the time of introduction of the cells.

In certain embodiments, the matrix is biodegradable and substantially uniform in composition.

In certain embodiments, the site comprises an incision or void made in a tissue, and the matrix is implanted into the incision or void. In certain embodiments, the site comprises a surgical incision or void made in a tissue, and the matrix is implanted into the incision or void.

In certain embodiments, the method comprises creating an open subcutaneous and/or an open dermal site in the subject, and implanting a matrix into the open subcutaneous and/or open dermal site in the subject.

In certain embodiments, the method comprises creating an open subcutaneous and/or an open dermal site in the subject, and implanting a biodegradable matrix into the open subcutaneous and/or open dermal site in the subject.

In certain embodiments, the matrix further comprises a seal.

In certain embodiments, the seal closes the site of implantation and/or reduces evaporative water loss from the site of implantation.

In certain embodiments, the matrix further comprises a non-biodegradable seal.

In certain embodiments, the seal comprises a polyurethane, a polyamide, a polyurethaneurea, a polypropylene or any other polymer capable of being formed into sheets or films, or silicone.

In certain embodiments, the matrix comprises a seal and the seal is removed prior to introduction of the cells. In certain embodiments, the seal is removed prior to introduction of the cells and the cells are introduced through the tissue exposed upon removal of the seal.

In certain embodiments, the method comprises creating an open dermal site in the subject, and implanting a biodegradable matrix into the open dermal site in the subject, wherein the matrix further comprises a non-biodegradable seal to close the site upon implantation of the matrix.

The size/volume of the matrix to be implanted may be selected, for example so as to be suitable to the site of implantation to be utilised and/or the number of cells to be implanted. In certain embodiments, the matrix comprises a volume in the range from 0.2 $cm^3$ to 20 $cm^3$. In certain embodiments, the matrix comprises a volume of in the range from 0.2 $cm^3$ to 5 $cm^3$. In certain embodiments, the matrix comprises a volume of in the range from 0.2 $cm^3$ to 0.8 $cm^3$. In certain embodiments, the matrix comprises a volume of 0.2 $cm^3$ or greater, 0.8 $cm^3$ or greater, 3.2 $cm^3$ or greater, or 5 $cm^3$ or greater. For example, the matrix for implantation may have a size from 1×1 cm with a 2-5 mm depth, a size of 2 to 4 cm by 2 to 4 cm with a 2-5 mm depth, up to a size of 10×10 cm with a 2-5 mm depth for use in the abdominal wall.

In certain embodiments, the matrix does not produce a substantial inflammatory reaction (local or systemic) when implanted. Methods for assessing inflammation are known in the art.

In certain embodiments, the number of cells for introduction comprises $1×10^3$ to $1.2×10^4$ islet equivalents per kg body weight of the subject. Typical final volumes of cells for islet transplantation are 1 to 7 $cm^3$ of cellular material.

In certain embodiments, the method comprises administering an immunosuppressive agent to the subject. In certain embodiments, the administering of the immunosuppressive agent comprises systemic administration of the immunosuppressive agent.

In certain embodiments, the administering of the immunosuppressive agent comprises local administration of the immunosuppressive agent in the region of the site of implantation or derived from the matrix. Methods for administering agents are known in the art.

In certain embodiments, the subject is a human subject. In certain embodiments, the subject is suffering from, or susceptible to, type 1 diabetes, type 2 diabetes, insulin resistance and pre-diabetes.

In certain embodiments, the subject is a subject undergoing pancreatectomy, so as to have a subsequent islet auto transplantation of their own islet cells back into their body.

Certain embodiments of the present disclosure provide a method of delivering a cell derived factor to a subject, the method comprising:
  implanting a biodegradable matrix into an intracutaneous and/or dermal site in the subject;
  allowing neovascularisation of the site with the implanted matrix to form a neovascularised site; and
  introducing cells producing a cell derived factor into tissue in the neovascularised site, thereby delivering the cell derived factor to the subject produced from the cells introduced into the site.

Certain embodiments of the present disclosure provide a method of delivering a cell derived factor to a subject, the method comprising:
  creating an open intracutaneous and/or an open dermal site in the subject;
  implanting a biodegradable matrix into the open intracutaneous and/or open dermal site in the subject, wherein the matrix further comprises a non-biodegradable seal to close the site upon implantation of the matrix;
  allowing neovascularisation of the site with the implanted matrix to form a neovascularised site; and
  introducing cells producing a cell derived factor into tissue in the neovascularised site, thereby delivering the cell derived factor to the subject produced from the cells introduced into the site.

In certain embodiments, a method as described herein is used to prevent and/or treat a disease, condition or state in a subject.

In certain embodiments, a method as described herein is used to prevent and/or treat type 1 diabetes, type 2 diabetes, insulin resistance and/or pre-diabetes in a subject.

Certain embodiments of the present disclosure provide a method of preventing and/or treating a disease, condition or state that would benefit of the introduction of cells that produce a cell derived factor.

Certain embodiments of the present disclosure provide a method of preventing and/or treating a disease, condition or state as described herein by implanting a matrix into a site in the subject to allow neovascularisation of the site with the implanted matrix, and introducing cells producing a cell derived factor into the site, thereby preventing and/or treating the subject.

Certain embodiments of the present disclosure provide a method of preventing and/or treating diabetes, pre-diabetes or insulin resistance in a subject, the method comprising:
  implanting a matrix into a site in the subject to allow neovascularisation of the site with the implanted matrix; and
  introducing cells producing, or capable of producing, insulin into the site, thereby preventing and/or treating the subject by delivering the insulin produced from the cells to the subject.

Examples of cells for introduction are as described herein. In certain embodiments, the cells comprise allogeneic cells. In certain embodiments, the cells comprise xenogeneic cells. Methods for obtaining cells for introduction into a subject are known in the art.

In certain embodiments, the cells are part of a heterogeneous (multi-cell) cluster such as the Islets of Langerhans, or comprise pancreatic beta cells and/or a progenitor cell type thereof.

Examples of sites for introduction of cells are as described herein. In certain embodiments, the site comprises an intradermal site or an intramuscular site.

Examples of matrices are as described herein. In certain embodiments, the matrix is biodegradable.

In certain embodiments, the matrix comprises one or more of a polyurethane, a collagen, a glycosaminoglycan, a collagen-GAG co-polymer and/or mixture, a mucopolysaccharide, a poly(alpha-hydroxy acid), a poly(lactic acid) and/or a structural isomer thereof, a polyglycolic acid and/or a structural isomer thereof, a chitosan, a polylactic-polyglycolic polymer, and a polycaprolactone.

In certain embodiments, the matrix comprises a biodegradable polyurethane.

Examples of introducing cells are as described herein. In certain embodiments, the introducing of the cells occurs after neovascularisation of the site.

In certain embodiments, the introducing of the cells occurs prior to vascularisation of the site. In certain embodiments, the introducing of the cells occurs during vascularisation of the site.

In certain embodiments, the site is partially or substantially vascularised at the time of introducing the cells. In certain embodiments, the site is partially vascularised at the time of introducing the cells. In certain embodiments, the site is substantially vascularised at the time of introducing the cells.

In certain embodiments, the matrix is partially or substantially replaced with tissue, at the time of introduction of the cells.

In certain embodiments, the matrix is partially or substantially replaced with neovascularised tissue at the time of introduction of the cells.

In certain embodiments, the matrix is permanently implanted in the site.

In certain embodiments, the matrix is partially or substantially innervated and vascularised, at the time of introductions of the cells.

In certain embodiments, the site comprises an incision or void made in a tissue and the matrix is implanted into the incision or void.

In certain embodiments, the method comprises creating an open intracutaneous and/or an open dermal site in the subject, and implanting a matrix into the open intracutaneous and/or open dermal site in the subject.

In certain embodiments, the method comprises creating an open intracutaneous and/or an open dermal site in the subject, and implanting a biodegradable matrix into the open intracutaneous and/or open dermal site in the subject.

In certain embodiments, the matrix further comprises a seal. In certain embodiments, the matrix further comprises a non-biodegradable seal. In certain embodiments, the seal comprises a polyurethane.

In certain embodiments, the seal closes the site of implantation and/or reduces evaporative water loss from the site of implantation.

In certain embodiments, the matrix comprises a seal and the seal is removed prior to introduction of the cells. In certain embodiments, the seal is removed prior to introduction of the cells and the cells are introduced through the tissue exposed upon removal of the seal.

In certain embodiments, the method comprises creating an open intracutaneous and/or an open dermal site in the subject, and implanting a biodegradable matrix into the open intracutaneous and/or open dermal site in the subject, wherein the matrix further comprises a non-biodegradable seal to close the site upon implantation of the matrix.

In certain embodiments, the matrix does not produce a substantial inflammatory reaction when implanted.

Examples of methods for introducing cells are as described herein. In certain embodiments, the introducing of the cells into the site comprises injection of the cells into the site. In certain embodiments, the introducing of the cells into the site comprises device assisted placement of the cells within the site.

In certain embodiments, the number of cells for introduction comprises $1 \times 10^3$ to $1.2 \times 10^4$ islet equivalents per kg body weight of the subject.

In certain embodiments, the introducing of the cells into the site comprises seeding of the cells into the matrix prior to neovascularisation.

Methods for assessing the efficacy of treatment are known in the art. For example, assessing the efficacy of treating diabetes may include one or more of restoration of blood glucose levels, c-peptide levels and amelioration of one or more symptoms of diabetes.

Certain embodiments of the present disclosure provide a method of preventing and/or treating diabetes, pre-diabetes or insulin resistance in a subject, the method comprising:
implanting a biodegradable matrix into an intracutaneous and/or dermal site in the subject;
allowing neovascularisation of the site with the implanted matrix to form a neovascularised site; and
introducing cells producing insulin into tissue in the neovascularised site, thereby delivering insulin to the subject produced from the cells introduced into the site.

Certain embodiments of the present disclosure provide a method of preventing and/or treating diabetes, pre-diabetes or insulin resistance in a subject, the method comprising:
creating an open intracutaneous and/or an open dermal site in the subject;
implanting a biodegradable matrix into the open intracutaneous and/or open dermal site in the subject, wherein the matrix further comprises a non-biodegradable seal to close the site upon implantation of the matrix;
allowing neovascularisation of the site with the implanted matrix to form a neovascularised site; and
introducing cells producing insulin into tissue in the neovascularised site, thereby delivering insulin to the subject produced from the cells introduced into the site.

Certain embodiments of the present disclosure provide use of a biodegradable matrix for preventing and/or treating a disease, condition or state as described herein.

Certain embodiments of the present disclosure provide use of a biodegradable matrix for implantation into a subject for preventing and/or treating diabetes, pre-diabetes or insulin resistance in the subject.

Certain embodiments of the present disclosure provide a combination product.

Certain embodiments of the present disclosure provide a combination product, the product comprising:
a matrix that when implanted into a site in a subject allows neovascularisation of the site with the implanted matrix; and
a device for introducing cells into the site.

In certain embodiment, the matrix comprises a synthetic matrix. In certain embodiments, the matrix comprises a natural matrix and/or a matrix derived from a natural product.

In certain embodiments, the matrix is a biodegradable matrix. In certain embodiments, the biodegradable matrix comprises a polyurethane.

In certain embodiments, the biodegradable matrix comprises a seal. In certain embodiments, the biodegradable matrix comprises a non-biodegradable seal. Examples of seals are as described herein.

Certain embodiments of the present disclosure provide a combination product, the product comprising:
a biodegradable matrix that when implanted into a site in a subject allows neovascularisation of the site with the implanted matrix; and
a device for introducing cells into the site.

Examples of devices are as described herein. In certain embodiments, the device comprises a syringe for injecting cells into the site.

Certain embodiments of the present disclosure provide use of a combination product as described herein for preventing and/or treating diabetes, pre-diabetes or insulin resistance in a subject.

Certain embodiments of the present disclosure provide a kit for use in a method as described herein.

Certain embodiments of the present disclosure provide a kit for delivering a cell derived factor to a subject, the kit comprising a biodegradable matrix that when implanted into a site in the subject allows neovascularisation of the site with the implanted matrix and optionally one or more reagents and/or devices for preparing and/or delivering cells that produce a cell derived factor to the site.

The kit may include one or more reagents, components, and devices as described herein, and/or instructions for performing a method as described herein.

For example, a kit may comprise the matrix, and one or more of enzymes, buffers, additives, stabilisers, diluents, culture media, agents, growth factors, consumables, and instructions.

Certain embodiments of the present disclosure provide a non-human animal producing an exogenous cell derived factor, the exogenous cell derived factor produced from cells introduced by a method as described herein.

The use of the non-human animal as an animal model for preventing and/or treating a disease, condition or state is as described herein.

Certain embodiments of the present disclosure provide a non-human animal producing an exogenous cell derived factor, the exogenous cell derived factor produced from cells introduced into a neovascularised site in the animal, the cells producing, or capable of producing, the exogenous cell derived factor, and wherein the neovascularised site is formed by implanting a biodegradable matrix into the site and allowing neovascularisation of the site with the implanted matrix.

Examples of cell derived factors are as described herein. In certain embodiments, the cell derived factor comprises insulin.

Non-human animals are as described herein. In certain embodiments, the non-human animal is an animal such as a non-human primate, a rabbit, a rat, a mouse, a dog, a cat, a horse, a cow, a sheep, a goat, or a pig. Other types of non-human animals are contemplated.

Certain embodiments of the present disclosure provide non-human animals having exogenous cells introduced into the animal by a method as described herein.

Certain embodiments of the present disclosure provide a non-human animal comprising exogenous cells introduced into a neovascularised site in the animal, the cells producing, or capable of producing, a cell derived factor, and wherein the neovascularised site is formed by implanting a biodegradable matrix into the site and allowing neovascularisation of the site with the implanted matrix.

Examples of cell derived factors are as described herein. In certain embodiments, the cell derived factor is insulin.

In certain embodiments, the exogenous cells comprise a heterogeneous (multi-cell) cluster such as the Islets of Langerhans, or pancreatic beta cells and/or a progenitor thereof.

Certain embodiments of the present disclosure provide use of a non-human animal as described herein to identify a treatment of diabetes, pre-diabetes or insulin resistance.

Certain exemplary embodiments are illustrated by some of the following examples. It is to be understood that the following description is for the purpose of describing particular embodiments only and is not intended to be limiting with respect to the above description.

Example 1—Creation of a Vascularized Skin Site for Islet Transplantation Using a Matrix Material Initially a de novo vascular bed is created by implanting a biodegradable scaffold or matrix material intracutaneously, which is designed to integrate, becoming a neo-dermis.

Treatment of Diabetes

Figure 1A:
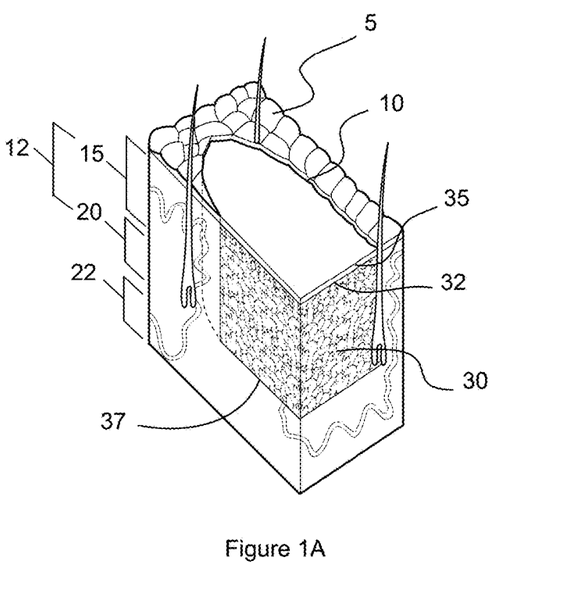
FIG. 1A-D shows a cross section schematic of the islet transplant process into a matrix derived vascular dermal bed in a patient at Day 0 and at stages 30 days and 100 days afterwards.

Patients with type-1 diabetes are identified using known protocols. Skin 5 consists of a thin superficial epidermis 15 and a thick deep dermis 20. In such patients a incision or opening 10 is made through the epidermis 15 and dermis 20 down to the level of the junction between dermis and the subcutaneous layer 22 (but not extending into the subcutaneous layer). This incision is to be created where there is a natural laxity of the skin (for example, in the skin of the medial side of the upper arm, in the groove between the biceps muscle and the brachialis muscle or in the skin in the flexion crease of the lower abdomen. This will create a space into which a matrix or scaffold 30 with a seal or superficial layer 35 may be implanted. A typical graft site of 4 cm$^2$ to 25 cm$^2$ is created 10, as shown in FIG. 1A, which is at day 0. The matrix material 30 is inserted in such a way that the seal 30 is approximately flush with the surface of the skin 5, although this is not essential. The bottom surface 37 of the matrix material 30 does not extend into the subcutaneous layer 22, so that the whole matrix is intracutaneous 12 (within the skin).

Isolation of islet cells for allo-transplantation or auto-transplantation is then undertaken as required by those skilled in the field using known procedures.

Figure 1B:
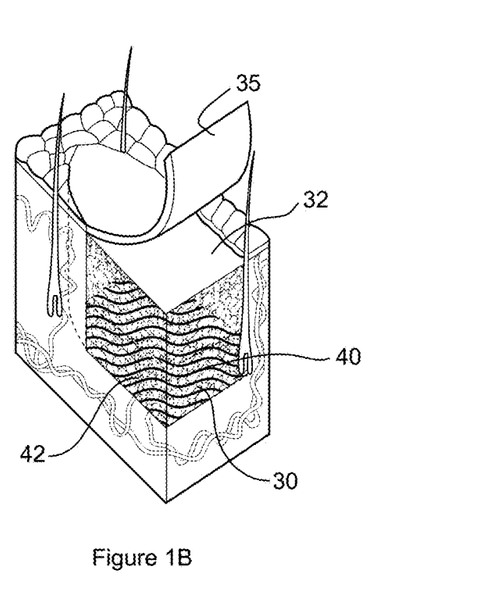
Figure 1C:
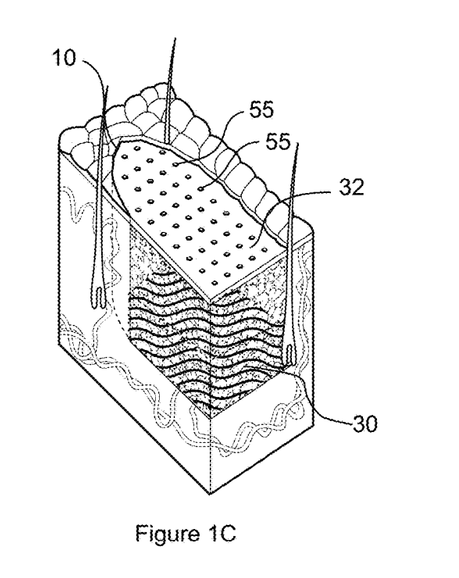
Figure 1D:
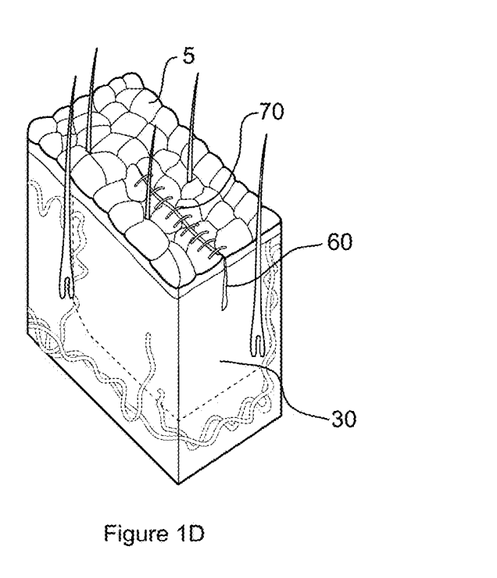

At approximately day 30, when isolated islet cells are available, the seal 35 or superficial layer (epidermal layer) covering the upper surface 32 of the matrix material 30 is carefully removed. As shown in FIG. 1B, the matrix material 30 has become vascularised to create a neovascularised area 40, in which the blood vessels 42 have penetrated into the matrix material 30 which provides a suitable environment for islet seeding. Islet cells are then directly seeded or injected into the now vascularised matrix material 30 by direct injection through the now exposed upper surface 32 of the matrix material 30, as shown in FIG. 3C with rows 55 of injection sites. The opening 10 is then closed by folding the matrix material 30 creating a V-formation 60 in cross-section and creating a linear wound, which can be secured 70 with sutures or staples as shown in FIG. 1D at 100 days, in which the opening 10 has healed and the functional islets cells reside within the matrix material for release of insulin to treat the patient.

Normal skin comprises a molecular dermis and a cellular epidermis. The matrix material forms a neo-dermis when implanted intracutaneously into a wound. The pore size (mean 200 micrometres), and the open-cell structure of the polyurethane foam (matrix material), encourages blood vessel ingrowth (neovascularisation) and fibroblast (dermal cell) invasion, with collagen deposition in such a way that surprisingly creates space and capacity for exogenous cell implantation. The collagen deposition within the matrix material neo-dermis is whorled, rather than laminar, and edematous. Thus, the loosely arranged polyurethane foam (matrix material) neo-dermis can surprisingly receive cellular implantation where the normal tightly structured collagen/elastin dermis will not. As such, the cellular application into the polyurethane foam neo-dermis of the matric material constitutes an intracutaneous (within the skin) application.

Figure 1F:
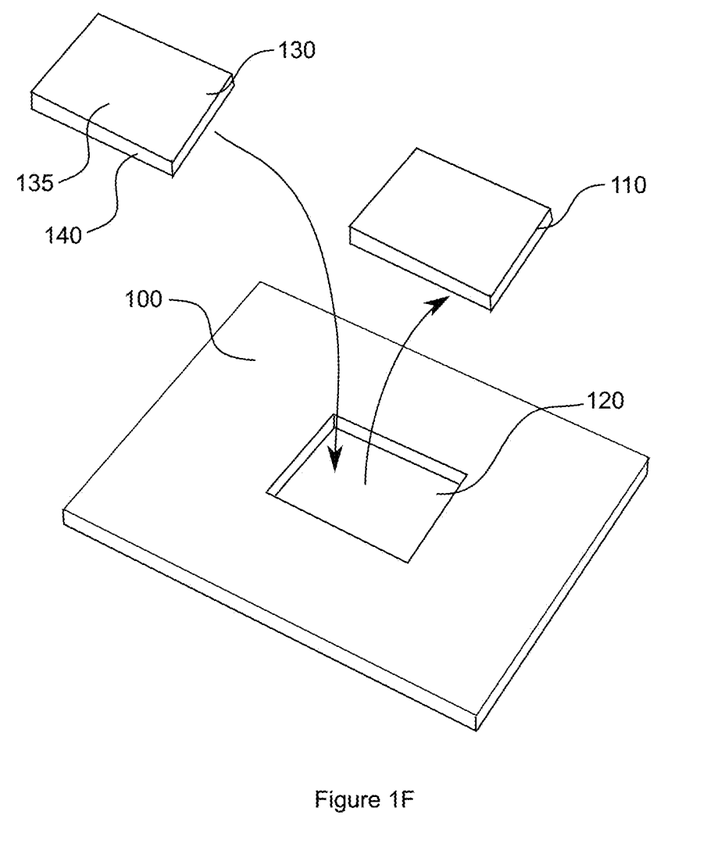
FIG. 1F shows a perspective view of a support matrix of the present invention with a removable inner section.

In an additional form of application, the matric material can comprise a primary (1°) matrix structure and a secondary (2°) matrix structure as shown in FIG. 1F in which there is a primary matrix material 100, that is inserted into the suitably sized opening in the patients skin, in the intracutaneous layer. The primary matrix material 100 has a removable inner section 110, which, after residing within the primary opening for the required time to allow neovascularisation, can be removed to leave a secondary opening 120. The inner section 110 is referred to as the secondary matrix material.

Suitably isolated islet cell material can then be inserted into the inner section 110 of the matrix material under controlled conditions to be loaded with the isolated islet cell by injection into its upper surface. This loaded inner section 110 can then be reinserted into the secondary opening 120 and the primary opening closed in the manner as described above.

Alternatively, the secondary matrix material 110 may be discarded and into the secondary opening 120 can be inserted a new separate secondary matrix material insert 130, which may be of the same matrix material as the in-situ primary matrix material 100 or may be of a different matrix material, which his pre-loaded with the appropriate cells to treat the patients condition. In this instance the new separate secondary matrix material insert 130 is pre-loaded with isolated islet cells that can be injected into the upper surface 135 or into the sides 140. This then allows for efficient loading of islet cells into the new separate secondary matrix material 130 in suitably controlled conditions and accurate placement into the opening 120 in the in-situ primary main matrix material 100. The vascularisation in the neovascularised zone of the primary main matrix material 100 immediately adjacent to the pre-loaded new separate secondary matrix material insert 130 and the open cell form of the matrix material allows the cellular material, in this case islet cells, to diffuse directly into the adjacent neovascularised zone, as well as allowing for vascularisation of the new separate secondary matrix material 130 to occur.

Insulin independence will be achieved with a total of >10,000 islet equivalents per kg of recipient body weight.

Blood glucose and c-peptide levels in the patient can then be subsequently monitored to assess islet function.

It is envisaged that the introduction of the cells in the manner described above will reduce the need for supporting immunosuppressive therapy.

In the event that it is considered necessary to use of immunosuppressive therapy to support the function of allotransplanted cells, the medial practitioner may begin immunosuppressive therapy, for example using the Edmonton protocol. Examples of typical immunosuppressive medications are daclizumab (Zenapax), sirolimus (Rapamune), and tacrolimus (Prograf). Examples of other immunosuppressive medications used in islet transplantation include antithymocyte globulin (Thymoglobulin), alemtuzumab (Campath), basiliximab (Simulect), belatacept (Nulojix), etanercept (Enbrel), everolimus (Zortress), and mycophenolate mofetil (CellCept, Myfortic).

Example 2—Kits and Products

Kits and products for use in the methods of the present disclosure are considered to fall within the scope of the present invention.

A kit may include one or more of the following components:

(a) A matrix or scaffold for implanting into a suitable site. For example, a 2-5 mm thick foam with an area of 4 $cm^2$ to 25 $cm^2$, and which is a biodegradable matrix produced from a polyurethane, optionally with a 150-μm thick, nonbiodegradable, microporous polyurethane sealing membrane bonded to the surface. Typically γ-irradiation sterilised and held in sealed packages.

(ii) Reagents for introducing cells, such as islets of Langerhans cells or pancreatic beta cells, into a subject, such as phosphate buffered saline.

(iii) A device for introducing cells into a subject, such as a suitable syringe for injection of cells into the desired vascularized site.

(vii) Instructions.

One or more of the components of the kit may be packaged in sterile form. Other components in a kit are contemplated.

Combination products including one or more of a matrix, a device for introducing cells and reagents are also contemplated. For example, a combination product may comprise a matrix for implantation and a device for introducing cells into the subject.

Methods

Animal Study

The study was conducted in a Good Laboratory Practice-accredited animal facility and approved by the local animal ethics committee. Large White/Landrace pigs (*Sus scrofa*—initial weight 25-30 Kg) were used in xenogeneic transplant experiments. While Westran pigs were used for isogenic transplants. Standard diet and general animal care standard operation procedures were followed throughout the study. All animals were fasted overnight before surgery. Intramuscular Co-Amoxyclav (Clavulox, 3.5 ml) post-surgery and oral (Clavulox, 2 tablets twice daily) throughout the postoperative transplant period. Those animals undergoing allogeneic or xenogeneic transplants were placed on an immunosuppressive regime consisting of 0.25 mg/kg of Tacrolimus and Mycophenolate (500 mg) twice daily, starting 1-2 weeks pre-transplant surgery.

Matrix Material

Using a porcine wound model as previously published (Dearman et al 2012). Matrix material (biodegradable temporising matrix BTM) was provided by PolyNovo Biomaterials Pty. Ltd (Port Melbourne, Victoria, Australia) and were transplanted on to the back flank of pigs. For this study, 2 mm thick, biodegradable, microporous polyurethane membrane matrix material bonded to the superficial surface seal. Four wounds of 4 cm×4 cm were surgically created, where the full thickness of the skin is removed to the level of the panniculus adiposus under general anaesthesia induced by intramuscular ketamine 1 mg/10 kg and maintained by 2.5% isofluorane via endotracheal intubation. The flank and back hair were clipped, then shaved, two wound sites were prepared on each flank equidistant (4 cm) from the spine with 4 cm between ipsilateral flank wounds. All marked wound margins were infiltrated subcutaneously with 0.5% lignocaine with 1:400,000 adrenaline to aid postoperative comfort and reduce blood loss. The surgical area was then prepared with povidone iodine. The wounds were dressed to reduce shear and minimize the trauma with Acticoat™ (Smith & Nephew Ltd, Hull, United Kingdom) to minimize infection; and held in place by Hypafix™ (BSN Medical GmBH, Hamburg, Germany). A cotton/fabric "combine" dressing was used to further protect site.

Islet Transplantation

The matrix material was allowed to integrate for 17-25 days prior to islet infusion. Islets were pelleted in polyethylene tubing (internal diameter 0.58 mm and outer diameter 0.965 mm) prior to removal of non-biodegradable seal from each wound site (delamination). Using a 2 mm steel rod a channel was created to allow for the insertion of the islet loaded cannula. A Hamilton winder syringe was then used to slowly infuse the islets into the created channel. A split skin graft was then taken from adjacent skin and placed over the wound. Surgical staples were used to hold the skin graft in place.

Xenogeneic Transplantation

Human islets isolated at a remote isolation centre were shipped to Adelaide where they were cultured for a maximum of 6 days in CMRL Complete media supplemented with 2 mM glutamax, 10 mM HEPES, pen/strep and 10% human albumin (Albumex 20, Red Cross of Australia). On day of transplant islets were washed with HBSS, prior to loading into cannula. Animals were humanely killed 7 days post transplantation.

Isogenic Transplantation

Neonatal Porcine islets were isolated from Westran Piglets by isolation centre at Westmead hospital as per previously published (Jimenez-Vera et al, 2015) and shipped to Adelaide, where they were placed into culture overnight prior to transplantation. Islets were transplanted into Westran receipts (40-50 kg) after washing with saline and loading into cannula. Saline alone was used as a transplant control. Animals were humanely killed at least 100 days post transplantation in long-term survival studies.

Immunofluorescence

Figure 2:
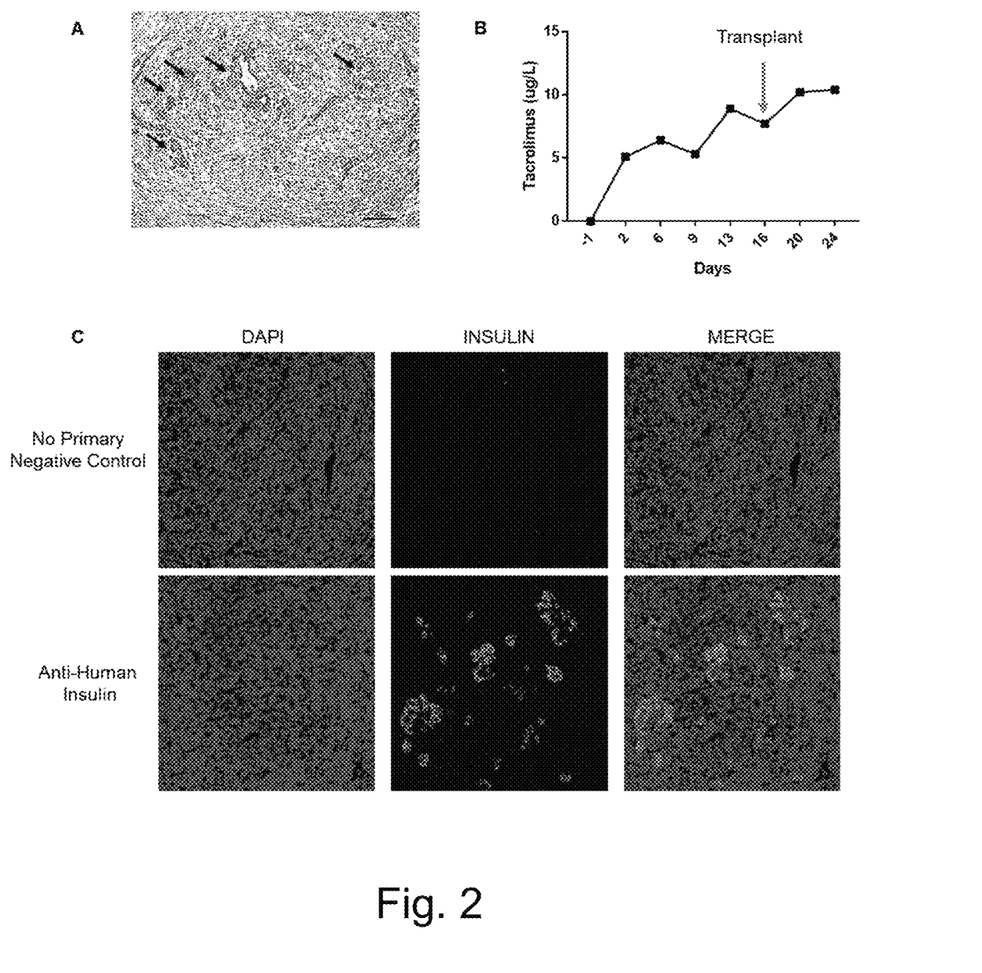

All tissues were fixed with 10% buffered formalin for at least 3 days prior to processing. Samples were paraffin embedded and section of 3 µm were cut and mounted onto superfrost plus slides. Sections were deparaffinised and re-hydrated prior to undergoing heat mediated antigen retrieval (Citrate buffer pH 6). Sections were incubated with Guineapig anti human-insulin antibody (AB7842; Abcam, Cambridge, UK) overnight as a primary anti-body alone at 2 µg/ml at 4° C. Insulin staining was then visualised with secondary goat anti-guineapig conjugated to Rhodamine fluorochrome (Jackson ImmunoResearch, Pennsylvania, USA) diluted 1 in 200 and incubated at room temperature in the dark for 1 h. Otherwise sections were co-stained with cross-reactive rabbit anti-mouse CD31 as a primary antibody overnight at a 4° C. (1:50 dilution of Ab28364, Abcam Cambridge, UK). A HRP-conjugated goat anti-rabbit polyclonal (1:2000) was used as the secondary antibody, before undergoing signal amplification with Tyramide Signal Amplification Kit as per manufacturer's instructions (Molecular probes, Thermofisher). As shown in FIG. 2, Human islets were transplanted into a pre-vascularised site of matrix material 24 days post implantation into immunosuppressed white landrace pig. A) Hematoxylin and eosin stain of transplanted section, arrows indicate possible islet architecture. Image taken at 100× magnification on the Nikon Eclipse. B) Tacrolimus level of transplanted pig, x-axis depicts the days post initiation of immunosuppression drug regimen consisting of Tacrolimus (0.25 mg/kg) and Mycophenolate (500 mg) twice daily. Red arrow indicates the day of transplant with human islets. C) Immunofluorescence staining of matrix material site 7 days post human islet transplantation, where 3 µm sections underwent antigen retrieval in citrate buffer prior targeting the insulin antigen with an goat anti-human insulin primary antibody, which was then visualised with goat anti-guineapig Rhodamine conjugated secondary (Red). Sections were counterstained with DAPI to visualise nuclei (Blue). Images were taken using the Olympus FV3000 confocal laser scanning microscope at a magnification of 200×.

Figure 3:
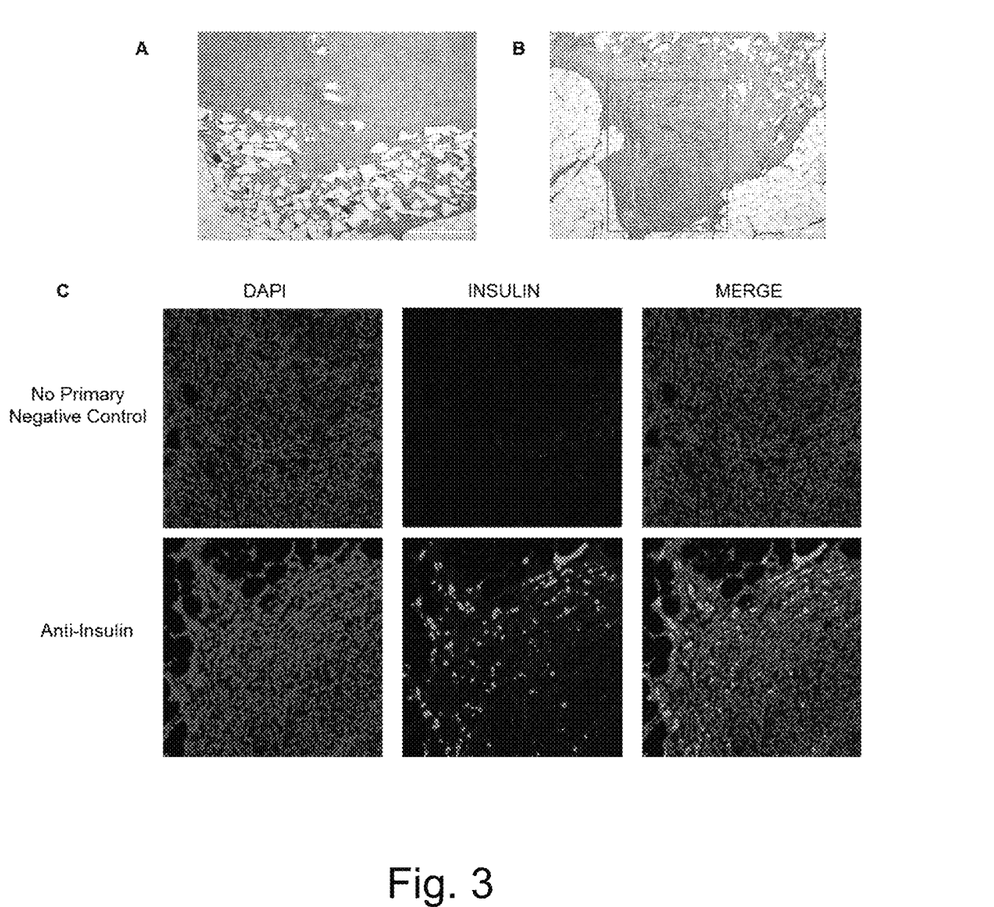
FIG. 3 shows visualisation of neonatal islets 101 days post islet transplantation into pre-vascularised matrix material.

Referring now to FIG. 3, Westran neonatal porcine islets were transplanted into a pre-vascularised matrix material site 18-24 days post implantation into isogenic Westran recipients. Saline infusion was used as a transplant control. A) Haematoxylin and eosin stain of Saline control transplant section, arrow indicates matrix material scaffold. Image taken at 40× magnification on the Nikon Eclipse. B) Haematoxylin and eosin stain of Neonatal islet transplant section 101 days post transplantation. Image taken at 40× magnification on the Nikon Eclipse. Red box indicates area of transplantation. C) Immunofluorescence staining of matrix material site 101 days post neonatal islet transplantation, where 3 µm sections underwent antigen retrieval in citrate buffer prior targeting the insulin antigen with an goat anti-human insulin primary antibody, which was then visualised with goat anti-guineapig Rhodamine conjugated secondary (Red). Sections were counterstained with DAPI to visualise nuclei (Blue). Images were taken using the Olympus FV3000 confocal laser scanning microscope at a magnification of 200×.

What we have seen is that by following the methods of the invention as described, the insertion of the islet cells in the intracutaneous layer resulted in more activity in producing insulin when compared to know models of islet cell transplantation, such as close to the liver or in a subcutaneous location. The increase in the activity of the islet cells in the intracutaneous layer was most unexpected.

Although the present disclosure has been described with reference to particular examples, it will be appreciated by those skilled in the art that the disclosure may be embodied in many other forms.

Reference to any prior art in this specification is not, and should not be taken as, an acknowledgment or any form of suggestion that this prior art forms part of the common general knowledge in any country.

As used herein, the singular forms "a," "an," and "the" may refer to plural articles (i.e., "one or more," "at least one," etc.) unless specifically stated otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The subject headings used herein are included only for the ease of reference of the reader and should not be used to limit the subject matter found throughout the disclosure or the claims. The subject headings should not be used in construing the scope of the claims or the claim limitations.

The invention claimed is:

1. A method of delivering a cell derived factor to a subject in need thereof, the method comprising:
    implanting a matrix into an intracutaneous site in the subject to allow neovascularisation of the implanted matrix in the intracutaneous site; and introducing cells producing a cell derived factor into the implanted matrix in the intracutaneous site, thereby delivering the cell derived factor to the subject from the cells introduced into the implanted matrix in the intracutaneous site, wherein the cell derived factor comprises insulin.

2. The method according to claim 1, wherein the cells comprise allogeneic cells.

3. The method according to claim 1, wherein the cells comprise islets of Langerhans cells, pancreatic beta cells and/or a progenitor cell type thereof.

4. The method according to claim 1, wherein the matrix is biodegradable.

5. The method according to claim 1, wherein the matrix comprises one or more of polyurethane, biodegradable polyurethane, collagen, glycosaminoglycan, collagen-GAG copolymer, collagen-GAG mixture, mucopolysaccharide, poly(alpha-hydroxy acid), poly(lactic acid), polyglycolic acid, chitosan, polylactic-polyglycolic polymer, and polycaprolactone.

6. The method according to claim 1, wherein the introducing of the cells occurs after neovascularisation of the implanted matrix in the intracutaneous site.

7. The method according to claim 1, wherein the matrix is implanted into an incision or void made in the intracutaneous site.

8. The method according to claim 7, wherein the matrix further comprises a non-biodegradable seal.

9. The method according to claim 8, wherein the seal comprises a polyurethane.

10. The method according to claim 9, wherein the seal closes the implanted matrix and/or reduces evaporative water from the implanted matrix.

11. The method according to claim 8, wherein the seal is removed prior to introduction of the cells.

12. The method according to claim 1, wherein the introducing of the cells into the implanted matrix comprises injection of the cells.

13. The method according to claim 1, wherein $1 \times 10^3$ to $1.2 \times 10^4$ islet equivalents per kg body weight of the subject are introduced into the subject.

14. The method according to claim 1, wherein the method comprises administering an immunosuppressive agent to the subject.

15. The method according to claim 1, wherein the subject is suffering from, or susceptible to, type 1 diabetes, type 2 diabetes, insulin resistance and pre-diabetes or is undergoing pancreatectomy.

16. A method of treating diabetes, pre-diabetes or insulin resistance in a subject, the method comprising: implanting a matrix into an intracutaneous site in the subject to allow neovascularisation of the implanted matrix in the intracutaneous site; and introducing cells producing insulin into the implanted matrix in the intracutaneous site, thereby treating the subject by delivering the insulin produced from the cells to the subject.

17. The method according to claim 16, wherein the cells comprise allogeneic cells or xenogeneic cells.

18. The method according to claim 16, wherein the cells comprise Islets of Langerhans, pancreatic beta cells and/or a progenitor cell type thereof.

19. The method according to claim 16, wherein the matrix is biodegradable.

20. The method according to claim 16, wherein the matrix comprises one or more of polyurethane, biodegradable polyurethane, collagen, glycosaminoglycan, collagen-GAG copolymer, collagen-GAG mixture, mucopolysaccharide, poly(alpha-hydroxy acid), poly(lactic acid), polyglycolic acid, chitosan, polylactic-polyglycolic polymer, and polycaprolactone.

21. The method according to claim 16, wherein the introducing of the cells occurs after neovascularisation of the implanted matrix.

22. The method according to claim 16, wherein the matrix further comprises a non-biodegradable seal.

23. The method according to claim 22, wherein the seal comprises a polyurethane.

24. The method according to claim 22, wherein the seal closes the implanted matrix and/or reduces evaporative water from the implanted matrix.

25. The method according to claim 22, wherein the seal is removed prior to introduction of the cells.

26. The method according to claim 16, wherein the introducing of the cells into the implanted matrix comprises injection of the cells.

27. The method according to claim 16, wherein $1 \times 10^3$ to $1.2 \times 10^4$ islet equivalents per kg body weight of the subject are introduced into the subject.

28. The method according to claim 16, wherein the introducing of the cells into the implanted matrix comprises seeding of the cells producing insulin into the matrix prior to the neovascularisation.

29. The method according to claim 16, wherein the method comprises administering to the subject an immunosuppressive agent.

30. A method of treating diabetes, pre-diabetes or insulin resistance in a subject, the method comprising: implanting a biodegradable and substantially uniform matrix into an intracutaneous site in the subject; allowing neovascularisation of the implanted matrix to form a neovascularised matrix; and introducing cells producing insulin into the neovascularised matrix, thereby delivering the insulin to the subject.

31. The method according to claim 30, wherein the matrix further comprises a non-biodegradable seal to close the intracutaneous site upon implantation of the matrix.

* * * * *